United States Patent [19]

Hiller et al.

[11] Patent Number: 5,398,698
[45] Date of Patent: Mar. 21, 1995

[54] PROCESS FOR PREPARING AN INTRAVAGINAL APPLICATION SYSTEM

[75] Inventors: Dietrich Hiller, Wiesbaden; Theophil Hornykiewytsch, Frankfurth am Main, both of Germany

[73] Assignee: Hoechst Aktiengesellschaft, Frankfurt am Main, Germany

[21] Appl. No.: 436,726

[22] Filed: Nov. 15, 1989

[30] Foreign Application Priority Data

Nov. 17, 1988 [DE] Germany .................. 38 38 815.4

[51] Int. Cl.⁶ ............................................. A61K 27/12
[52] U.S. Cl. ........................... 128/830; 604/890.1; 604/55; 128/832
[58] Field of Search ............... 128/832, 830, 833, 834, 128/839; 604/890.1, 891.1, 55

[56] References Cited

U.S. PATENT DOCUMENTS

| | | | |
|---|---|---|---|
| 3,920,805 | 11/1975 | Roseman | 128/832 X |
| 3,993,072 | 11/1976 | Zaffaroni | 128/833 X |
| 3,993,073 | 11/1976 | Zaffaroni | 128/833 X |
| 3,995,633 | 12/1976 | Gougeon | 128/832 |
| 3,995,634 | 12/1976 | Drobish | 128/832 |
| 4,012,497 | 3/1977 | Schopflin . | |
| 4,016,251 | 4/1977 | Higuchi et al. | 128/832 X |
| 4,043,339 | 8/1977 | Roseman . | |
| 4,292,965 | 10/1981 | Nash et al. | 128/833 |
| 4,311,543 | 1/1982 | Strickman et al. | 128/832 X |
| 4,331,651 | 5/1992 | Reul et al. . | |
| 4,447,373 | 5/1984 | Chappell et al. . | |
| 4,526,578 | 7/1985 | Wong | 128/832 X |
| 4,585,451 | 4/1986 | Millar | 128/832 X |
| 4,623,593 | 11/1986 | Baier et al. | 623/11 |

FOREIGN PATENT DOCUMENTS

| | | |
|---|---|---|
| 2603191 | 3/1988 | France . |
| 3728671 | 3/1988 | Germany . |
| 217370 | 5/1987 | New Zealand . |
| 2168257 | 6/1986 | United Kingdom ............... 128/832 |

*Primary Examiner*—Robert A. Hafer
*Assistant Examiner*—David J. Kenealy
*Attorney, Agent, or Firm*—Finnegan, Henderson, Farabow, Garrett & Dunner

[57] ABSTRACT

In the process for preparing an intravaginal application system for the controlled release of substances, a milled sheet of silicone rubber containing the substances is inserted into one mold component of a split mold. The core of the system is arranged on this milled sheet and is covered with a second milled sheet of the same type. The mold is then closed and the milled sheets are vulcanized at a maximum temperature of 120° C.

12 Claims, No Drawings

PROCESS FOR PREPARING AN INTRAVAGINAL APPLICATION SYSTEM

The invention relates to a process for preparing an intravaginal application system for the controlled release of substances, the application system comprising an elastic core with a sheathing containing the substances. The invention further relates to the application system itself.

Therapeutic systems for the vagina of an animal generally comprise a core which is free from active substances, and is primarily responsible for the stability and flexibility of the system, and a polymeric sheathing—the matrix—which contains the active substances which are to be released and determines their rate of release. DE 3,728,671 A1 discloses a process for preparing a device of the type initially mentioned in which the previously molded core of polyamide, appropriately centered in an injection mold, is sheathed with injection-moldable silicone rubber which contains progesterone. The rubber is cured at temperatures of 180° C. to 230° C. At this temperature, the incorporated progesterone melts, the melting point of the α-modification of the latter being about 130° C. and that of the β-modification being about 121° C. It is disadvantageous that the β-modification arises preferentially when the progesterone melt is cooled to room temperature. The latter modification partially escapes in an uncontrolled manner from the matrix and is deposited as a powder-like crystalline layer on the surface of the silicone rubber. At the same time, it partially recrystallizes into the α-modification. As a result of both occurrences, the rate of release from the device varies all the time during storage. Moreover, the high processing temperature severely limits the selection of a material which is suitable for the preparation of the core which is free from active substances. The material must have relatively high heat resistance, so that no distortions of the core occur during curing of the liquid silicone rubber.

The object of the invention is to provide a remedy in this case.

The object is achieved by the invention through a process for preparing an intravaginal application system which comprises inserting a milled sheet of silicone rubber containing the substances in one mold component of a split mold, arranging the core of the system on the milled sheet and covering it with a second milled sheet, then closing the mold and vulcanizing at a maximum temperature of 120° C.

A mixture of silicone rubber and substances comprising therapeutically effective components and components affecting the properties of the silicone, can be used as the milled sheet. α-Progesterone can be used as a therapeutically effective component. Silicone oil, esters of lauric acid, glycerol, silicon dioxide, caprylic/capric acid triglycerides and/or esters of these acids may be used as components which can affect the properties of the silicone rubber. In order to ensure good location, a low loss rate and minimum irritation of the mucous membrane in the vagina, a core with a resilience of 5 to 15N, which comes fully into contact with the mucous membrane, should be used for the system. Core material with the required resilience has thicknesses of 2 to 15 mm.

The system itself is one wherein a milled sheet of silicone rubber with a kick-off temperature between 60° and 120° C. is arranged on a core having a resilience of 5 to 15N, the milled sheet containing α-progesterone and the substance affecting the silicone rubber.

The advantages achieved from the invention are essentially to be seen in that the active substance does not melt when the silicone rubber is cured, so that it is impossible for different modifications with different release rates to be formed. As core, moreover, instead of the relatively inelastic polyamide, which has to be provided with elastic joints in order to increase its elasticity, the more elastic, less heat-resisting polypropylene can be used, which in contrast to polyamide does not have to be dried.

Cores made from polypropylene with a T-shape are particularly suitable for the application system according to the invention. Depending on the intended use, the shank (web) is 50 to 140 mm high and the flange is 40 to 200 mm wide. The length of web and flange can be 5 to 30 mm and the thickness can be 2 to 15 mm.

In the process according to the invention, a solid silicone rubber is used, into which the substances, such as in particular active substances, for example progesterone, substances which affect the release of the active substances from the silicone matrix (European Patent 0,013,949), and substances which affect the physical-mechanical properties of the silicone matrix, are incorporated by milling on a roll mill. This operation lasts for about 15 to 30 minutes. If one of the components which are to be incorporated by milling is liquid, this can be formed into a paste with silicon dioxide or with another inert medium, for example a pigment, before being incorporated by milling. A milled sheet of variable thickness is obtained, according to the nip width of the roll mill. A corresponding milled sheet of thickness 2 to 10 mm, is inserted into one mold component of a heatable split mold, the core is arranged upon it and is covered with a second milled sheet of the same thickness. After closing the mold, the latter is heated to the vulcanization temperature, which, when progesterone is used, should be between 70° C. and 120° C., preferably between 80° C. and 110° C. A silicone rubber whose vulcanization temperature (kick-off temperature) lies in this range, must therefore be selected. The vulcanization time is about 4 to 8 minutes.

We claim:

1. An application system for the controlled release of substances, comprising an elastic core with a sheathing containing these substances, wherein a milled sheet of silicone rubber with a kick-off temperature of between 60° and 120° C., and containing the substances is arranged on a core having a resilience of 5 to 15N, the milled sheet containing α-progesterone and substances which modify the properties of the silicone rubber.

2. An application system for the controlled release of substances, comprising an elastic core and a sheathing on said core of a silicone rubber, said silicone rubber having a kick-off temperature in the range of from about 60° to about 120° C. and containing said substances.

3. An application system for the controlled release of substances as recited in claim 2, wherein said substance is α-progesterone.

4. An application system for the controlled release of substances as recited in claim 3, wherein said sheathing further comprises substances which modify the properties of the silicone rubber.

5. An application system for the controlled release of substances as recited in claim 4, wherein said substances which modify the properties of the silicone rubber are selected from the group consisting of silicone oil, esters of lauric acid, glycerol, silicon dioxide, caprylic/capric acid triglycerides and esters of caprylic/capric acid.

6. An application system for the controlled release of substances as recited in claim 3, wherein said core has a resilience of 5 to 15 Newtons.

7. An application system for the controlled release of substances as recited in claim 2, wherein said core comprises polypropylene.

8. An application system for the controlled release of substances as recited in claim 3, wherein said core comprises polypropylene.

9. An application system for the controlled release of substances as recited in claim 8, wherein said core has a T-shape comprising a shank portion and a flange portion.

10. An application system for the controlled release of substances as recited in claim 9, wherein the shank is from about 50 mm to about 140 mm high and the flange is from about 40 mm to about 200 mm wide.

11. An application system for the controlled release of substances as recited in claim 10, wherein said shank is from about 5 mm to about 30 mm high and said flange is from about 5 mm to about 30 mm wide.

12. An application system for the controlled release of substances as recited in claim 11, wherein the thickness of said shank and flange are within the range of from about 2 mm to about 15 mm.

* * * * *